US010738348B2

(12) United States Patent
O'Farrell et al.

(10) Patent No.: US 10,738,348 B2
(45) Date of Patent: Aug. 11, 2020

(54) NUCLEIC ACID ANALYSIS METHOD AND APPARATUS (71) Applicant: ALTRATECH LIMITED, Limerick (IE)

(72) Inventors: Brian O'Farrell, Watergrasshill (IE); Timothy Cummins, Cratloe (IE)

(73) Assignee: ALTRATECH LIMITED, County Clare (IE)

( * ) Notice: Subject to any disclaimer, the term of this patent is extended or adjusted under 35 U.S.C. 154(b) by 0 days.

(21) Appl. No.: 15/101,254

(22) PCT Filed: Dec. 10, 2014

(86) PCT No.: PCT/EP2014/077185
§ 371 (c)(1),
(2) Date: Jun. 2, 2016

(87) PCT Pub. No.: WO2015/091139
PCT Pub. Date: Jun. 25, 2015

(65) Prior Publication Data
US 2016/0304941 A1    Oct. 20, 2016

(30) Foreign Application Priority Data
Dec. 12, 2013 (EP) ..................................... 13197025

(51) Int. Cl.
*C12Q 1/68* (2018.01)
*C12Q 1/6825* (2018.01)
(Continued)

(52) U.S. Cl.
CPC ........... *C12Q 1/6825* (2013.01); *C12Q 1/682* (2013.01); *C12Q 1/6827* (2013.01);
(Continued)

(58) Field of Classification Search
CPC ........ C12Q 2563/149; C12Q 2565/519; C12Q 2563/143; G01N 27/3276; G01R 27/2605; G01R 33/1269
See application file for complete search history.

(56) References Cited

U.S. PATENT DOCUMENTS 5,164,319 A * 11/1992 Hafeman ............. G01N 27/227
                                                            204/400
6,548,311 B1 * 4/2003 Knoll ................... C12Q 1/6825
                                                            205/777.5
(Continued)

FOREIGN PATENT DOCUMENTS

CN    102471051 A    5/2012
WO    99/27367 A1    6/1999
(Continued)

OTHER PUBLICATIONS

International Search Report issued in PCT/EP2014/077185; dated Jul. 1, 2015.
(Continued)

*Primary Examiner* — Betty J Forman
(74) *Attorney, Agent, or Firm* — Brown Rudnick LLP; Thomas C. Meyers (57) ABSTRACT

Methods of detecting target nucleic acid is a sample are described. A first probe is attached to first beads, and the first beads are placed in the sample so that any target nucleic acid attaches to the first probe. A second probe also attaches to the target nucleic acid so that any of the target nucleic acid links or "tethers" the first and second probes. A capacitive sensor detects capacitance of the beads and processes capacitance data to quantify target nucleic acid presence in the sample. The second probe may be immobilised on the sensor surface. Alternatively the second beads are introduced into the sample with the second probe attached, and the extent of
(Continued)

SEQ ID No. 1                              SEQ ID No. 2

```
                5'                    3'      5'                               3'
Probe1<-5'- CGA TCC CCT ATC AGC C        T TCT GGT GTT GAC AAC ATG ACT ACT G->Probe2
           ::: ::: ::: ::: ::: :         : ::: ::: ::: ::: ::: ::: ::: :::  :
      3'- GCT AGG GGA TAG TCG GGG TGA AGA CCA CAA CTG TTG TAC TGA TGA CGG TGA TTA TGA GTA TCG ...
```

SEQ ID No. 3 tethering of the first beads to the second beads is indicative of the extent of target NA present.

23 Claims, 7 Drawing Sheets

(51) Int. Cl.
G01R 33/12 (2006.01)
C12Q 1/682 (2018.01)
C12Q 1/6827 (2018.01)
C12Q 1/6837 (2018.01)
C12Q 1/6888 (2018.01)

(52) U.S. Cl.
CPC ......... *C12Q 1/6837* (2013.01); *C12Q 1/6888* (2013.01); *G01R 33/1269* (2013.01); *C12Q 2600/124* (2013.01); *C12Q 2600/156* (2013.01)

(56) References Cited

U.S. PATENT DOCUMENTS

| | | | |
|---|---|---|---|
| 2001/0055763 A1* | 12/2001 | Singh | B82Y 15/00 435/6.11 |
| 2002/0168663 A1 | 11/2002 | Phan et al. | |
| 2004/0005582 A1* | 1/2004 | Shipwash | G01N 33/54366 435/6.19 |
| 2004/0058389 A1* | 3/2004 | Wang | G01N 33/54326 435/7.1 |
| 2004/0078219 A1* | 4/2004 | Kaylor | G06F 19/3418 705/2 |
| 2006/0040286 A1 | 2/2006 | Mirkin et al. | |
| 2006/0205061 A1* | 9/2006 | Roukes | B01L 3/5027 435/287.2 |
| 2006/0205093 A1* | 9/2006 | Prins | G01N 33/54333 436/526 |
| 2007/0132043 A1* | 6/2007 | Bradley | B82Y 10/00 257/414 |
| 2008/0160622 A1* | 7/2008 | Su | G01N 1/4044 436/86 |
| 2009/0127589 A1* | 5/2009 | Rothberg | C12Q 1/6874 257/253 |
| 2010/0267162 A1 | 10/2010 | Kartalov et al. | |
| 2011/0053788 A1* | 3/2011 | Bamdad | B01J 13/00 506/9 |
| 2012/0073986 A1* | 3/2012 | Jackson | C12Q 1/001 205/775 |
| 2013/0046257 A1* | 2/2013 | Beck | A61K 38/20 604/307 |

FOREIGN PATENT DOCUMENTS

| | | |
|---|---|---|
| WO | 01/09388 A1 | 2/2001 |
| WO | 2007/106579 A2 | 9/2007 |
| WO | 2011/017660 A2 | 2/2011 |

OTHER PUBLICATIONS

Chavidi Venkata Prasad et al.; "Formulation and Characterization of Sodium Alginate g-Hydroxy Ethylacrylate Bio-Degradable Polymeric Beads: In Vitro Release Studies"; J Polym Environ; Jan. 29, 2012; pp. 344-352; vol. 20; Springer Science+Business Media, LLC.

International Preliminary Report on Patentability and Written Opinion of the International Searching Authority; PCT/EP2014/077185 dated Jun. 14, 2016.

Extended European Search Report (EESR) dated Oct. 23, 2017 from corresponding European application No. 17178871.4-1403; 7pp.

Chinese Office Action dated Nov. 22, 2018 issued in corresponding Chinese Patent Application No. 201480075478.9; with translation; 12pp.

\* cited by examiner

```
        SEQ ID No. 1                    SEQ ID No. 2
      5'             3'      5'                              3'
Probe1<-5'- CGA TCC CCT ATC AGC C   T TCT GGT GTT GAC AAC ATG ACT ACT G ->Probe2
            ::: ::: ::: ::: ::: :   : ::: ::: ::: ::: ::: ::: ::: ::: :
       3'- GCT AGG GGA TAG TCG GGG TGA AGA CCA CAA CTG TTG TAC TGA TGA CGG TGA TTA TGA GTA TCG ...

SEQ ID No. 3
```

Vessel 2

Fig 5

CMOS IC

Fig 6

CMOS IC

Fig 7

CMOS IC

Fig 8

CMOS IC

Fig 9

CMOS IC

NUCLEIC ACID ANALYSIS METHOD AND APPARATUS

The invention relates to a method and apparatus for analysing microbiological entities such as nucleic acid in a sample.

Real time diagnostics for nucleic acids (NA) such as DNA and RNA have been mooted for many years, but practical, applied and functional systems are scarce. Most existing systems are lab-based and involve NA modification with enzymes and chemical or fluorescent labels. This requires skilled laboratory technicians, and bulky expensive base units such as laser optical detectors. While such systems claim high sensitivity (e.g. detecting <100 target DNAs), in practice, they require amplification reactions (e.g. qPCR) where the target is copied up to a billion times before reliable detection. Testing more than one analyte at a time requires multiple parallel tests or a combination in one reaction (multiplex), further increasing the complexity of the chemistry. Amplification bias between different targets is a serious problem for multiplex assays as the efficiencies of PCR for each gene can vary by up to ~30%. Amplification steps require pure templates, because any co-extracted inhibitors such as humic acid may cause false negatives while, conversely, cross-contamination can cause false positives. Amplification steps involve complex chemistry; long enzymatic incubation times or thermal cycling. Both sample purification and amplification demand the integration of pumps, valves, filters, heaters, coolers or Peltier devices into microfluidic devices and/or into base units. Thermocycling without bubble formation in a microfluidic device is a particular problem. Enzymes used in amplification often cause issues with surface adsorption, creating problems for controlling the effective concentration of enzyme in the reaction; limiting the types of materials which can be used in microfluidics; and necessitating surface treatments in some cases. Complex chemistry requires complex technology, making it difficult for such systems to be used in remote field locations.

US2006/0205093 (Philips) describes use of particles with microbiological entities and applying a mechanical stress to bindings so that some bindings are disrupted and others are not.

The invention is directed towards providing direct, robust, sequence-specific and rapid detection of DNA or RNA, without complex chemistry and amplification steps. Multiplex detection and quantification would also be highly desirable.

SUMMARY OF THE INVENTION

According to the invention, there is provided a method of detecting a target microbiological entity in a sample, the method comprising the steps of:
providing a first probe attached to first beads;
placing said first beads in the sample so that any target microbiological entity attaches to said first probe;
providing a second probe which also attaches to said target microbiological entity so that any of said target microbiological entity links said first and second probes; and
detecting capacitance of said beads and processing capacitance data to quantify target microbiological entity presence in the sample.

In one embodiment, the second probe is immobilised on the sensor surface. In one embodiment, the second probe is a self-assembled monolayer on a fixed surface.

In one embodiment, the second probe is a self-assembled monolayer on a bead.

In one embodiment, said monolayer is a PNA monolayer which has a neutral charge.

In one embodiment, the sensor comprises a TSV chip having a planar sensor surface, and the sample is deposited on to said top surface.

In one embodiment, second beads are introduced into the sample, said second beads having the second probe attached, and the extent of tethering of the first beads to the second beads is indicative of the extent of target microbiological entity present. In one embodiment, the sample is pooled over the sensor.

In one embodiment, at least some beads are magnetic or paramagnetic. In one embodiment, the first beads are magnetic or paramagnetic, application of a magnetic field causing said first beads to act as transport beads which convey second beads which are tethered to the first beads by the target microbiological entity.

In one embodiment, the extent of tethering between the first and second beads is quantified by the sensor, wherein the sensor is calibrated to quantify the volume of beads according to dielectric performance of the beads. In one embodiment, difference of capacitance of the sample with only first beads present compared to sample with both first and second beads present is processed to provide a measure of target microbiological entity presence.

In one embodiment, the sensor has an analyte channel and a negative channel and the sensor is calibrated so that the same capacitance is detected in both channels if there is no target microbiological entity present in the analyte. In one embodiment, the microbiological entity is a nucleic acid and the calibration is for a single-base difference.

In one embodiment, the sensor surface supports an immobilised second probe and wherein second beads are introduced into the sample, said second beads having the second probe attached. In one embodiment, the second beads have a size in the range of 0.5 µm to 5 µm, and preferably 1.0 µm to 3.0 µm.

In one embodiment, the beads are magnetic and the analyte is magnetically stirred. In one embodiment, the beads are introduced so that the extent of tethering which occurs is proportional to the amount of target microbiological entity, and the number of second beads drawn from one location to another is proportional to the amount of target microbiological entity, and the sensor detects the number of second beads to indicate the extent of target microbiological entity.

In one embodiment, the method comprises the steps of magnetically removing tethered first and second beads, so that un-tethered second beads are isolated, and the sensor detects the number of second beads as being indicative of the amount of target microbiological entity.

In one embodiment, at least some of the beads are magnetic, and a magnetic field is applied to perform magneto-separation of the beads. In one embodiment, the magnetic field is moving.

In one embodiment, the microbiological entity is a nucleic acid and multiple target nucleic acids or loci are targeted, in which:
  a. for genes or loci A, B and C: $1_A + 1_B + 1_C = X3$ signal
  b. for genes or loci A and B: $2_A + 2_B = X2$ signal.

In one embodiment, the method does not distinguish between multiple genes such as A, B and C and assumes that each confer equal information about the question of interest. In one embodiment, A, B and C are SNPs which are all considered to be equally desirable in an animal being bred for a correlated trait such as milk production, and the sensor response is calibrated to indicate if an the animal is likely to have a particular characteristic such as being likely to produce quality milk yields.

In one embodiment, the combination of genes represent known mutations which are liable to lead to a particular genetic disease.

In one embodiment, the microbiological entity is a nucleic acid and anti-sense strand is also targeted such that non-complementary forward probes (F1 and F2) target slightly different loci on the sense and anti-sense strands of the same gene rather than different genes. Both sense and anti-sense strands are captured from the lysate and transported downstream.

In one embodiment, the sense and anti-sense strands do not interact with each other and cannot reform, and immobilised probes complementary to the R locus for both the sense ($R_{Fc}$) and anti-sense strand ($R_{Rc}$) are present but physically separated so the probes do not bind to each other. In one embodiment, each probe is at a different location, first beads carrying sense strands bind in one location and those carrying anti-sense strands bind in another location. In one embodiment, two types of bead covered in non-complementary reverse probes (R1 and R2) are incubated with the larger beads and NA, captured, transported over a sensor chip, released, agitated and bind to the correct SAM on each of a plurality of capacitance sensors (21, 22). In one embodiment, gene expression levels are ascertained by comparing the number of sense strand beads bound (sense strand DNA and mRNA) with the number of antisense strand beads bound (antisense strand DNA only).

In one embodiment, a sequence specific F locus is used for first bead tethering to NA in the lysate and multiple second bead R loci ($R_1$, $R_2$, $R_3$) are used.

In one embodiment, multiple target nucleic acids or loci are targeted ($F_1$, $F_2$, $F_3$) and second bead R loci ($R_1$, $R_2$, $R_3$) bind to each of the respective NAs.

In one embodiment, the R loci are selected to provide additional sequence specificity to that conferred by the first beads but primarily amplify the signal for each nucleic acid captured by a first bead.

In one embodiment, the $R_1$, $R_2$ and $R_3$ loci are distinguished from each other downstream by magneto-separation of different size second beads.

In one embodiment, the $R_1$, $R_2$ and $R_3$ loci are distinguished from each other downstream using different immobilized second probes on different sensors (10, 11).

In one embodiment, the method is performed to detect truncated DNA or specifically RNA products, in situations where mutations in cells causing stop codons or insertion/deletion events causing frame shifts result in the truncation of mRNA transcripts and failure of the correct protein to be translated.

In one embodiment, at least some beads are adapted to degenerate over the sensor with application of heat to the extent that at least some of the beads become integral In one embodiment:
the second beads are stable in aqueous solution but break down when moved into the solution over the sensor, and/or
the second beads contain elements (e.g. salt) which change the capacitance of the solution, and/or
breakdown of the second beads releases a fine debris of particles (e.g. ferrite) which increases the change in capacitance immediately over the surface of the capacitance sensor.

In one embodiment, the microbiological entity includes NA, and wherein separation of second beads from first beads and NA complexes is accomplished by the second beads being coated by a thin layer of wax upon which Streptavidin is coated, heating is performed to melt the wax to undermine the binding of the Streptavidin on the R-bead from the underlying paramagnetic bead so that the core of the second beads become separated.

In one embodiment, the microbiological entity includes NA, and wherein PNA probes complementary to those on the second beads are used to separate second beads from first beads.

In one embodiment, said separation is performed at approximately room temperature.

In one embodiment, when the second beads are over the sensor the analyte contains the complementary PNA probes and these displace the target nucleic acid due to preferential PNA-PNA binding and release the nucleic acid.

In one embodiment, first beads with different NAs bound pick up multiple second beads, and the second beads are melted to separate them from the first beads and they are free to mix with a sensor array which has multiple immobilised probes.

In one embodiment, the second beads are covered in PNA probe and adhere to the immobilised probe.

In one embodiment, the immobilised probes are alternated such as row by row to ensure equal opportunity for each second bead to bind to an immobilised probe.

In one embodiment, there are multiple different targets to be detected concurrently.

In one embodiment, PNA probes allow beads to become tethered to larger beads by nucleic acid during cell lysis.

In another aspect, the invention provides a detection apparatus comprising:
means for providing a first probe attached to first beads;
means for placing said first beads in the sample so that any target microbiological entity attaches to said first probe;
means for providing a second probe which also attaches to said target microbiological entity so that any of said target microbiological entity links said first and second probes; and
a capacitive sensor for detecting capacitance of said analyte and processing capacitance data to quantify target microbiological entity presence in the analyte.

DETAILED DESCRIPTION OF THE INVENTION

Figure 1:
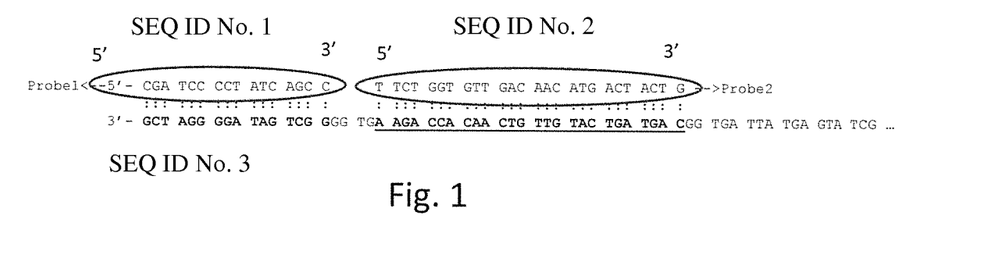
FIG. 1 shows sequences allowing attachment of an R-bead ("Reporter beads") to a T-bead ("Transport bead") using target DNA.

The invention provides methods and apparatus for processing samples so that target nucleic acid (typically DNA) is made identifiable and quantified in a simple and quick manner without need for amplification. Specificity is provided by a sandwich assay of two probes binding at two different positions on the same NA. This exploits existing assays for PCR and real-time PCR which have sequence-specific forward and reverse primers. An example is the EURL "Horse-DNA" (*Equus caballus*) testing protocol (February 2013). This identifies a specific probe sequence and forward and reverse primers to be used in detecting an 87 base-pair target mitochondrial DNA sequence (FIG. 1). These probe sequences have been carefully designed to be species-specific. These same sites are targeted by our two probes.

Figure 2A:
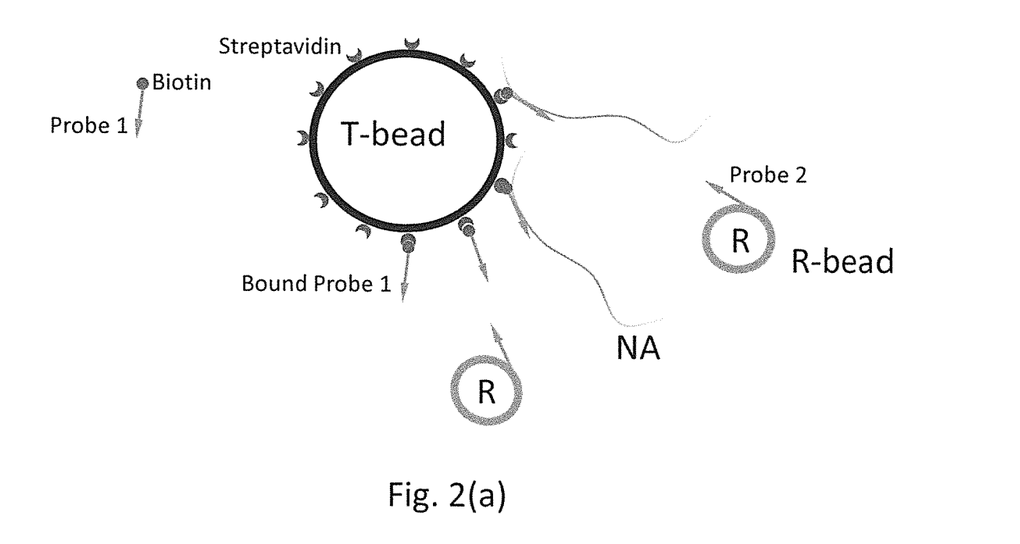
FIG. 2a shows simplex NA on T-bead with R beads.
Figure 2B:
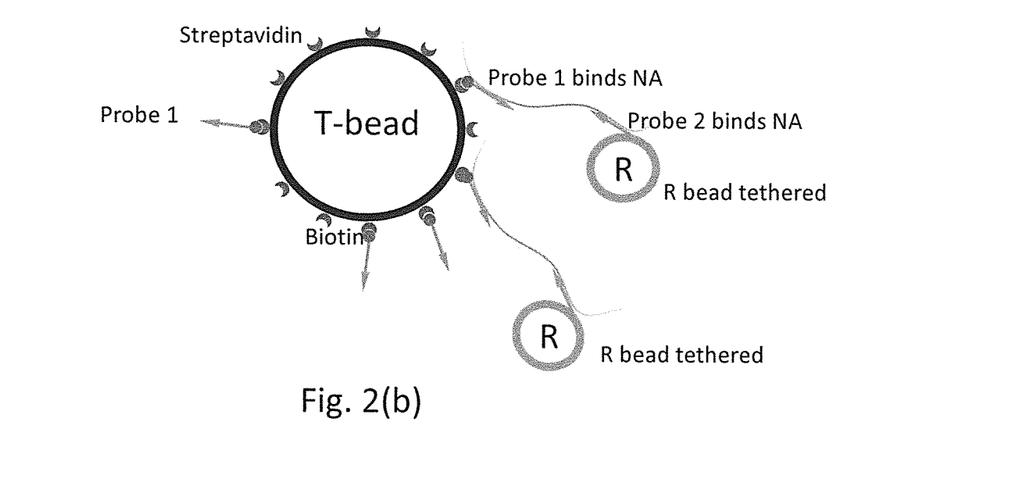
FIG. 2b shows simplex T and R beads tethered.

The biotinylated first probe is attached to a streptavidin-coated 2.8 μm transport or "T-bead", as per Homes (U.S. Pat. No. 5,512,439) for example (which describes removal of target single strand DNA or RNA from a lysate by hybridising them with complementary oligonucleotide DNA probes which are attached to magnetic beads). However, in this invention, PNA probes are used instead of DNA probes. The second probe is attached to a second, smaller (1.0 μm) paramagnetic reporter bead ("R-bead"). The T-beads with attached NA are introduced to a vessel containing deionised water and R-beads. As the R-beads are in solution, this improves encounter rate with any target NA. The R-beads are paramagnetic so mixing is further improved using agitation by an external magnet, e.g. circular movement of coaxial motor magnets such as Apex 18×14×20 mm. These R-beads become attached to the corresponding NA. Binding of the two probes across the same NA results in the T-bead and R-beads being tethered (FIGS. 1, 2*a*, 2*b*). Multiple, smaller R-beads may be tethered to the same T-bead by a corresponding number of target NAs (FIG. 2*b*). To improve test sensitivity, this assay can also be done in parallel for negative (no DNA) and positive (*E. caballus* mtDNA) samples (FIGS. 3 to 10).

Figure 5:
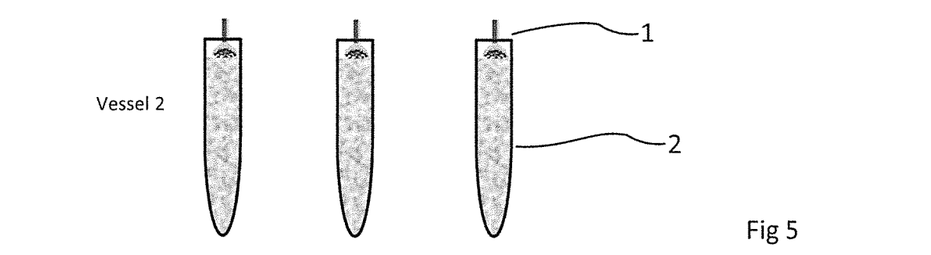

After 5 minutes of incubation, all T and R beads are drawn to the bottom of the vessel by a strong magnet. This takes about 1 minute. A plastic-coated inverted funnel tip 1 with a smaller magnet inside is then introduced at the top of the vessel (2 in FIG. 5), as shown in FIG. 5, for 2 minutes. This attracts the larger T-beads but not the unbound R beads. A coaxial magnet moving around the tube agitates and creates a magnetic gradient. This magneto-separation is achieved because paramagnetic T- and R-beads of 2.8 μm and 1.0 μm respectively, in the same liquid medium, exposed to the same magnetic field and with the same magnetic susceptibility, experience a magnetic moment proportional to their radius cubed but a drag force which is directly proportional to their radius. The T-beads and R-beads accelerate towards their terminal velocity at which the drag increases to the point at which there is zero acceleration. The T-beads will consistently have a much faster terminal velocity. The R-beads will require far longer to get from one point to another given the same magnetic field for a given time.

T-beads and any bound R-beads tethered to them are clumped at the tip 1 and removed. Empirical evidence suggests a force of greater than 500 pN is needed to break DNA-DNA base-pair bonds. The number is higher for PNA-DNA. Therefore the smaller R beads are easily dragged along by the larger T-beads. This tethering can only occur if the target NA is present, therefore the number of tethered R-beads is a direct indicator of the number of target NA's present.

This number of beads can be determined in a number of ways, for example by drawing them through a capillary optical particle counter as disclosed by Girvin et al in U.S. Pat. No. 5,684,585, or by capacitance tomography as described by W Q Yang "Hardware design of electrical capacitance tomography systems", Measurement Science Technology Vol 7 1996.

Figure 6:
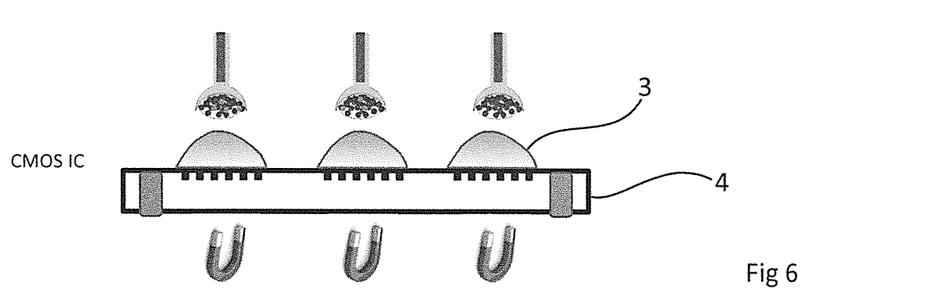
Figure 7:
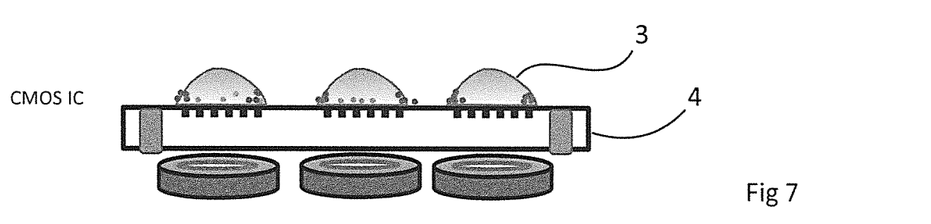
Figure 8:
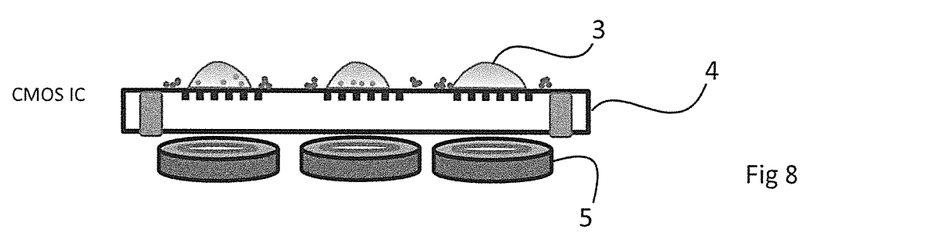
Figure 9:
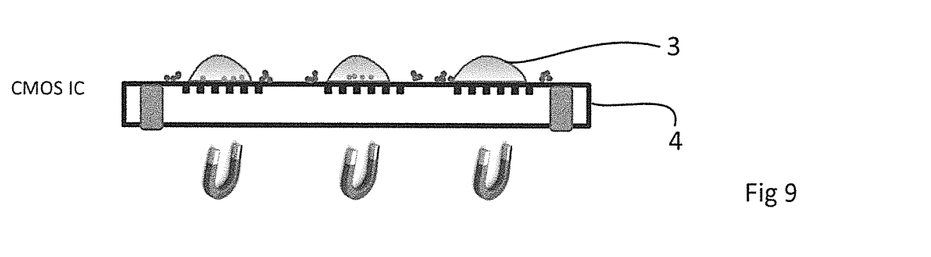

In this embodiment, the T-beads and R-beads are placed onto a large droplet 3 of DI water which is on top of a CMOS capacitance sensor IC 4 (FIGS. 6 and 7).

The IC 4 is formed with through-silicon-vias (TSV), such as described in U.S. Pat. No. 8,513,061 for example. These are etched from the back of the silicon wafer, then backfilled with copper. This brings all input-output connections to the rear of the IC 4, eliminating bond wires and surface topography, greatly facilitating the application and movement of droplets and beads to the sensor surface. As shown in FIGS. 6 to 10 there is a smooth planar top surface for receiving the sample.

The positive and negative versions of the assay are also shown. The droplets are heated to the melting temperature of the R-bead probe and NA complex (e.g. 60° C.) by on-chip or under-chip heaters. This releases the R-beads. Circular magnets are now introduced around the sensor which pull the T-beads away to the circumference of the sensor and holds them in place as the droplet begins to evaporate (FIGS. 7-8), but leave the unbound R-beads trapped within the droplet over the sensor. The droplet now contains only the R-beads. Small magnets are now applied beneath the sensor, which pool the R-beads at the bottom of the droplet on the sensor surface. The bulk of the R-beads, which have a lower dielectric constant to the DI water 3, provide a very clean signal which is directly proportional to the amount of target NA in the original sample. If horse DNA is in the analyte, this can be detected by the comparative change in capacitance at the analyte, positive and negative sensors.

Figure 10:
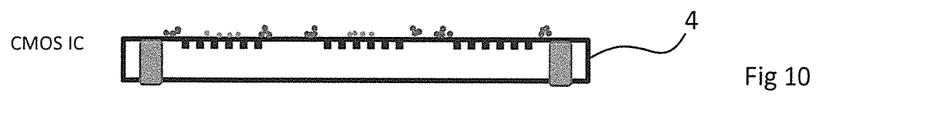

This procedure takes approximately 1 to 2 minutes. After 3 to 4 minutes, the droplet has completely evaporated (FIG. 10). The beads have a higher dielectric constant than air, giving a different capacitance reading for each of the analyte, positive, and negative sensors. These "wet" and "dry" capacitance readings give a cross-check correlation for better specificity and sensitivity. In another variation, the beads can be formed of beeswax which melts at about 55° C., releasing a solute such as salt when the IC is heated. This changes the dielectric constant of the liquid droplet, further enhancing sensitivity.

The R-beads may alternatively be non-magnetic such as silica particles, large protein molecules, or composite materials. An example of the latter is a beeswax degenerative bead which deforms and/or melts (e.g. at 55° C.) to create an organic region of low dielectric constant along the sensor surface, or releases a solute such as salt. This changes the liquid dielectric constant, further assisting capacitive detection of the reporter beads.

Figure 2C:
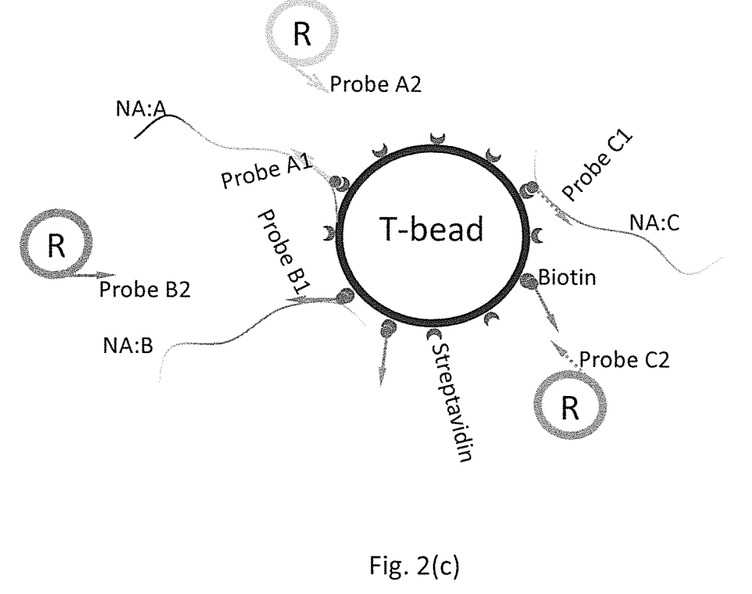
FIG. 2c shows multiplex NA on a T-bead with R beads.
Figure 2D:
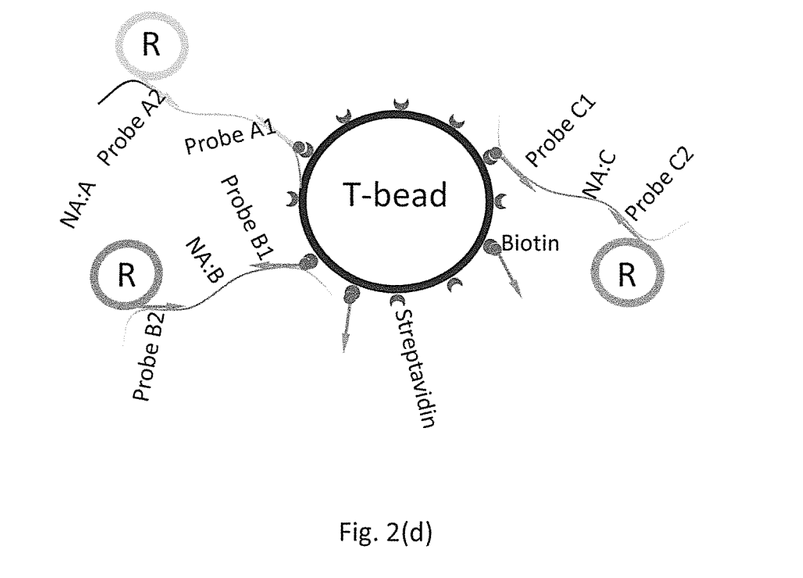
FIG. 2d shows multiplex T and R beads tethered.
Figure 3A:
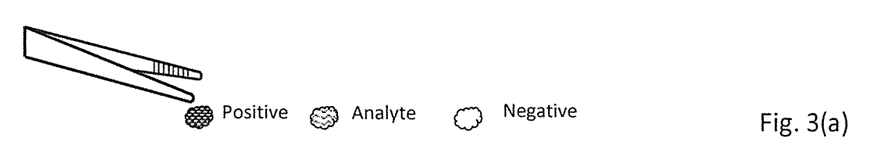
FIGS. 3a, 3b, 4a, 4b, and 5 to 10 are a series of views showing an analysis method.
Figure 3B:
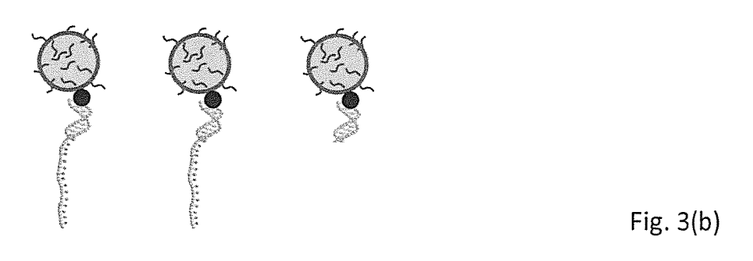
Figure 4A:
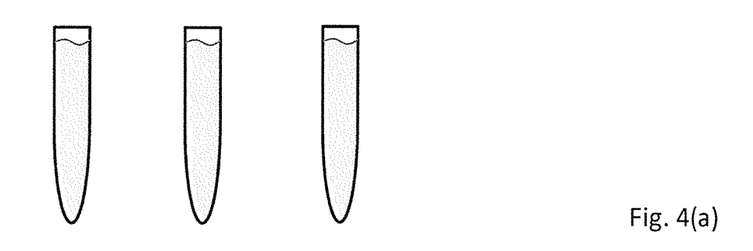
Figure 4B:
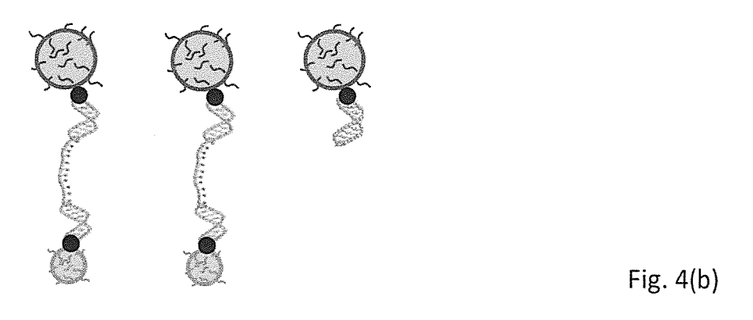
Figure 11:
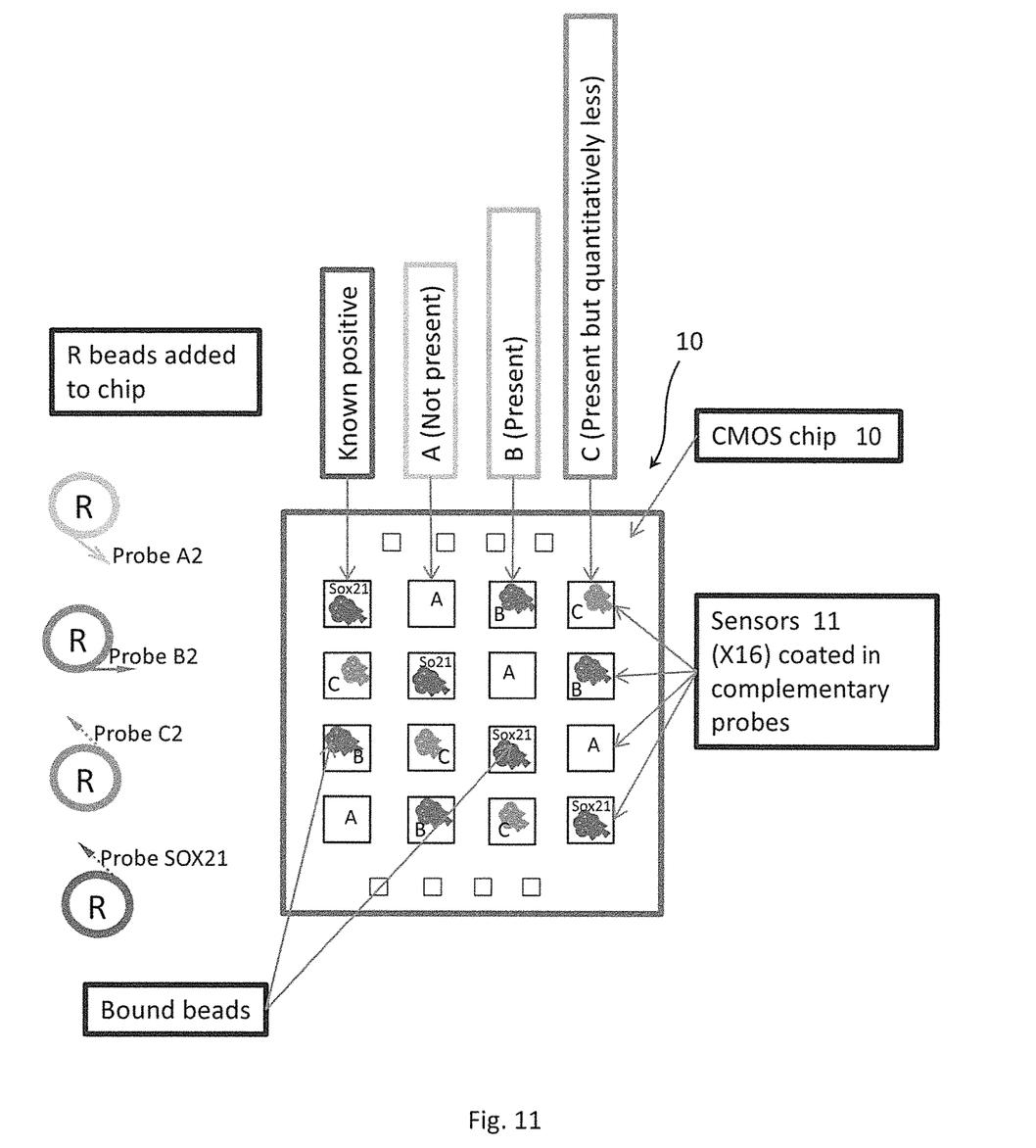
FIG. 11 shows a quantitative multiplex assay of R beads tethered to different SAMs sitting on sensors on a CMOS capacitance chip.

A multiplex embodiment of the invention is described below. This follows a very similar principle to the simplex assay but differs in that multiple NAs are bound to the same T beads by multiple probes (FIGS. 2*c*, 2*d* and contrast with FIGS. 2*a*, 2*b*). Depending on the type and number of NAs captured on the T beads, a directly proportional number of the complementary R beads are captured from a mix of R beads. As shown in FIG. 11 there is a TSV CMOS sensor 10 with sixteen sensing regions 11. The mix of R beads is then transported over the sensor 10 where they are separated from the T beads and are free to mix above the sensor surface. This employs self-assembled-monolayers (SAM) formed on multiple sensor 11 surfaces, where each SAM has a unique sequence-specific probe embedded or tethered to the sensor surface which is complementary to the probe on respective, free R beads. The R beads, if present, are bound on the correct sensor surface (FIG. 11). The change in capacitance at each sensor is, thus, proportional to the number of each R bead type captured and to the number of NAs in the original sample (FIGS. 2c, 2d, 11).

A sample is prepared by performing target enrichment on a sample lysate, Homes (U.S. Pat. No. 5,512,439). This lysis step occurs in a separate mesofluidic or microfluidic vessel. Four distinct biotinylated PNA probes capture four distinct NAs ($L_A, L_B, L_C, L_D$) according to their relative proportions in the lysate. One of the PNA probes targets a highly conserved non-coding region upstream of the SOX21 gene. This serves as a positive control for the assay. The other three PNA probes target loci known to vary in the population. The NAs are captured by the PNA probes by Watson-Crick bonding which in turn are bound to streptavidin-coated paramagnetic T-beads. Paramagnetic T-beads are magnetically concentrated in a suitable receptacle (which can be manually moved and engaged with each vessel as per vessel. The T-beads are magnetically drawn into an incubation vessel. The incubation vessel contains paramagnetic beads—smaller 1.0 µm 'reporter' beads—"R-beads" (FIG. 2c). The R-beads are divided into four equal proportions ($R_A, R_B, R_C, R_D$) each of which is coated in a second PNA probe complementary to the respective downstream site on NAs $L_A, L_B, L_C,$ and $L_D$. NAs on the T-beads will capture the complementary R-beads. More than one R-bead can be captured on each T-bead.

The paramagnetic beads are drawn down to the base of the vessel using a magnet. The magnet is now removed and another magnet is engaged.

Paramagnetic T-beads and bound R-beads are magnetically concentrated in and removed. The receptacle is manually moved and engaged with another vessel. This vessel leads to the surface of the CMOS sensor. The paramagnetic beads are drawn down to the base of the vessel using a magnet. The vessel is heated to break one or more of the probes allowing the tethering of T and R-beads. The R-beads of each type are now unbound. The magnet is now removed and another magnet is engaged. The T-beads are separated from the R-beads, captured in the receptacle and removed from the vessel. The R-beads remaining are magnetically agitated to provide mixing over the surface of the CMOS sensor. As noted above the CMOS sensor 10 contains four separate sensor regions 11 each covered in four distinct SAMs with probes complementary to each of the four bead types. The beads become bound on the surface of the correct SAM. The number of beads bound on each SAM is proportional to the original amount of NA in the lysate. The change in capacitance registered by the corresponding sensor is directly proportional to the number of beads. The sensor corresponding to the positive control of the SOX21 gene should always contain bound R beads. The relative proportions of R beads bound to the three other corresponding sensors give both qualitative and quantitative information about genetic variation in the sample.

Note: All probes may contain suitable spacers (e.g. PEG) and ligands (e.g Biotin) to provide for good interactions with nucleic acids, SAMs, substrates (e.g. silicon nitride or paramagnetic beads or wax)

R-Bead Decoupling

The entire assay may also be carried out isothermally. This is accomplished by having a solution of PNA probes in a vessel complementary to the T-bead PNA probes at the relevant positions on the four loci ($L_A, L_B, L_C, L_D$). PNA-PNA binding is preferred to PNA-NA binding. The PNA probe in solution invades the PNA-NA duplex holding the NA to the T-bead and allowing the NA and bound R-bead to be freed. The unzipping of the PNA-NA duplex is facilitated by having an overhang on this original PNA probe which is not complementary to the NA. This is then loose. A new PNA probe complementary to this overhang and the remaining probe sequence, binds and the invasion of the PNA-NA duplex is more efficient.

Quantitative Genetic Marker Index

In another assay there is a single sensor and no SAMs. The loci targeted ($L_A, L_B, L_C, L_D$):

a. For genes or loci A, B and C being present: $1_A+1_B+1_C=X3$ signal
b. For genes or loci A and D: $1_A+1_D=X2$ signal This technique cannot distinguish between A, B, C and D and assumes that each confer equal information about the question of interest. For instance, A, B, C and D may be four genetic markers for invasive insect species which are not distinguishable by eye from native species. The presence of any one such species indicates a problem. Similarly, the four loci may represent known mutations which are liable to lead to genetic disease. The presence of one or more such mutations in an animal may make it desirable to cull the animal over another animal testing negative for all such mutations. Conversely, the four loci may be SNPs which are all considered to be equally desirable in an animal being bred for a correlated trait such as milk production. The amount of signal from a capacitance based assay, as described above, generated in this application may be correlated with the animal being likely to produce quality milk yields.

Using existing amplification based methods such as endpoint PCR or LAMP, it would be impossible to tell the difference between the presence of one SNP and two SNPs. A qPCR approach using different labelled probes would be at least semi-quantitative but has all the disadvantages outlined earlier. As the method of the invention is direct and quantitative, assays which treat each SNP or target sequence as additive can return an index of the quality of a farm animal. This type of information will help with in line decision making in animal husbandry. As the technique uses direct quantification and simply using the amount of tissue sampled (e.g. standardised 1 $mm^3$ punch of tissue from animal ear) gives a baseline for DNA in the sample, it is possible to "count" multiple SNPs. Two SNPs being present should give twice the signal as one and so on.

Truncated Transcript Detection

In this embodiment, following from the multiplex assay above, three of the four R bead loci are all on one mRNA of interest. Mutations in cells causing stop codons or insertion/deletion events causing frame shifts result in the truncation of mRNA transcripts and failure of the correct protein to be translated. This type of mutation is important in many forms of cancer. Crucially, a critical oncogene could be targeted using this system and detect de novo mutations which cause shortening of the transcript. Truncated transcripts are the main causative factor for heriditary BRCA breast cancer risk. Where equal numbers of R-beads are captured on each of the three sensors, full transcripts are observed. Where transcripts are truncated, we observe reduced binding of the most downstream R-beads. A control is provided in the expression of a housekeeping gene such as SOX21.

Anti-Sense Strand Targeting and Gene Expression

Figure 12:
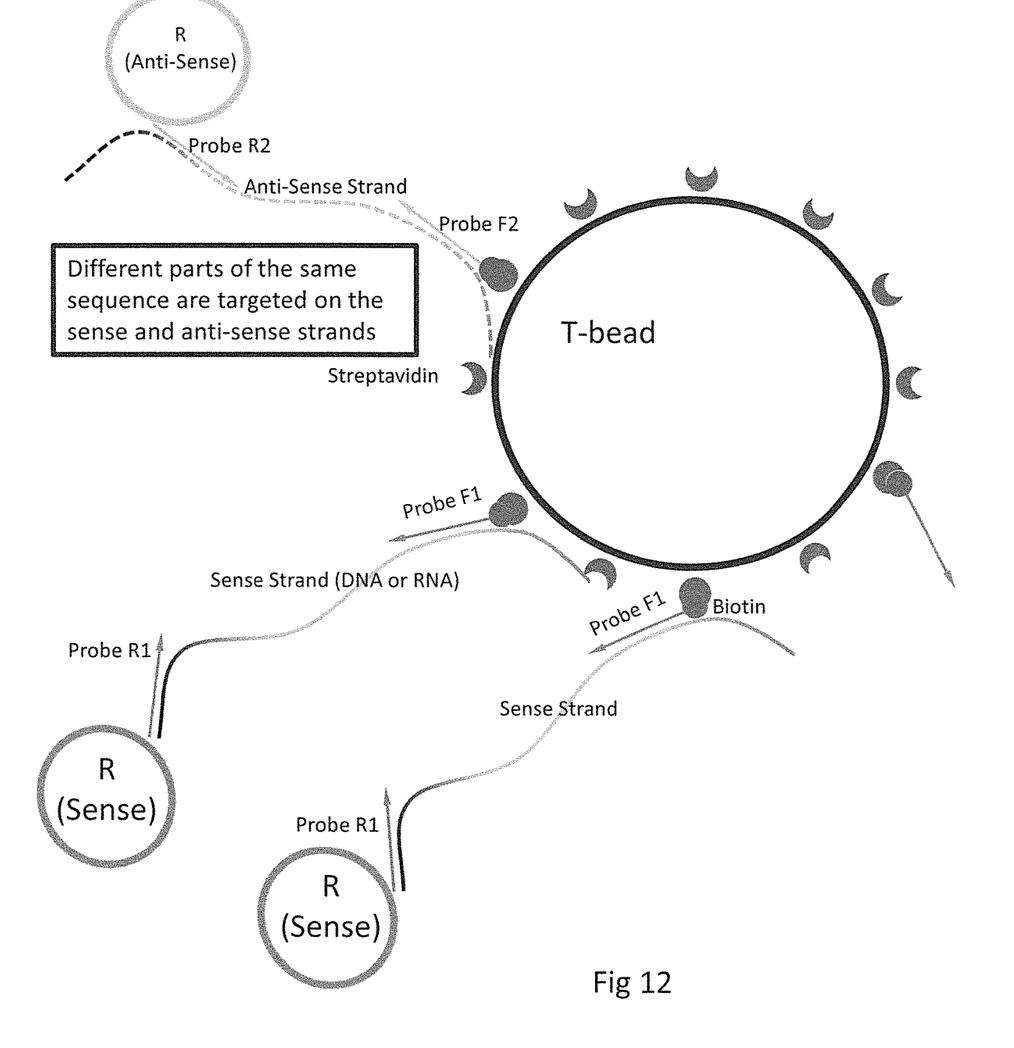
FIGS. 12 and 13 show a sensor and a mechanism for targeting of sense and anti-sense strands.
Figure 13:
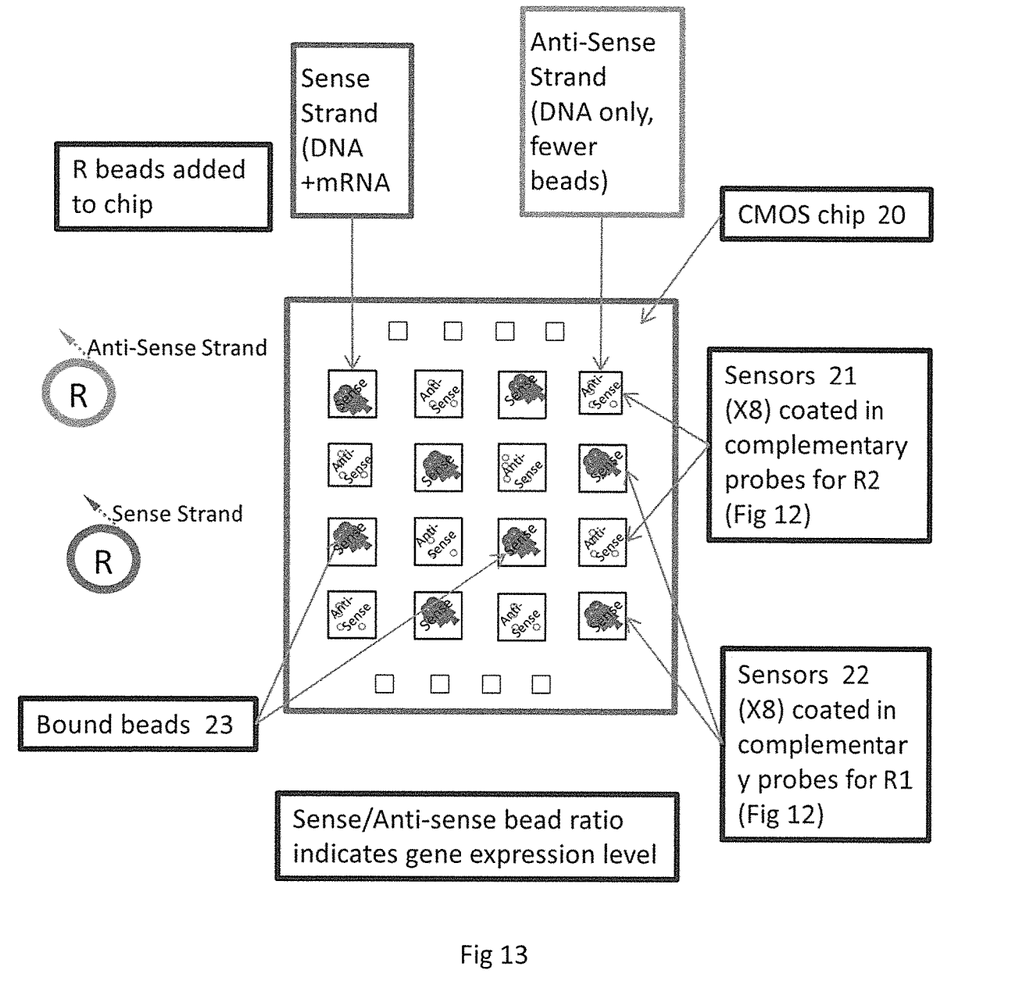

A variation of the multiplex assay allows targeting of the sense and anti-sense strands. Sense strand NA includes DNA and the more numerous mRNA whereas anti-sense NA will only include DNA. Non-complementary forward probes (F1 and F2, FIG. 12) target slightly different loci on the sense and anti-sense strands of the same gene rather than different genes. Both sense and anti-sense strands are captured on T beads. Similarly, two types of R bead covered in non-complementary reverse probes (R1 and R2, FIG. 12) are incubated with the T beads and NA, captured, transported over a sensor chip 20, released, agitated and bind to the correct SAM on each capacitance sensor 21, 22 (FIG. 13). Anti-sense strand-specific R beads detected provide a baseline for the amount of DNA in the sample. The number of sense strand-specific R beads should be more numerous and reflect the number of sense strand DNAs and mRNA. By comparing the signal on sense and anti-sense strand, it is possible to get an accurate and direct measure of gene expression levels for the gene of interest using this technique. In a simplex assay, as per the horse example, the same strategy would double the number of R beads captured and improve sensitivity.

T-Bead and R-Bead Tethering in Lysis Vessel

In this embodiment, T and R bead tethering takes place further upstream in a lysing vessel, shortening overall analysis time. R-beads coated in covalently-bonded PNA probes are added during a cell lysis step in Chelex solution (5-20% w/v) and become tethered using the target NA to T-beads immediately. During the subsequent magnetic removal step, R-beads are only removed from the lysis vessel if tethered to T-beads thereby providing for specificity and quantification of target nucleic acids as described in various embodiments above.

The invention is not limited to the embodiments described but may be varied in construction and detail. It is not essential that the target be NA. For example, it could alternatively be a protein, antigen, bacteria, virus or any other microbiological entity.

The invention claimed is:

1. A method of detecting a target microbiological entity in a crude sample with a detection apparatus comprising:
    a capacitive sensor to detect said target microbiological entity in said crude sample;
    a mesofluidic or microfluidic first vessel to receive said crude sample, into said first vessel are placed first beads, which are magnetic or paramagnetic;
    a second vessel for containing second beads, which are magnetic or non-magnetic; and
    a third vessel leading to a surface of said capacitive sensor,
    the method comprising:
    providing a first probe attached to said first beads;
    placing said first beads in said crude sample in said first vessel so that said target microbiological entity attaches to said first probe;
    magnetically removing said first beads to said second vessel containing said second beads, which have a second probe attached, to which said target microbiological entity attaches, thereby tethering said first and second beads, wherein an extent of said tethering is indicative of an extent of said target microbiological entity;
    applying a magnetic field causing said first beads to act as transport beads, which convey said tethered second beads, which are tethered to said first beads, to said third vessel leading to said surface of said capacitive sensor;
    releasing said tethered second beads from said first beads to provide released second beads and magnetically removing said first beads, wherein said capacitive sensor comprises a plurality of immobilized probes including self-assembled-monolayers formed on multiple sensor surfaces of said capacitive sensor, in which each self-assembled-monolayer has a unique sequence-specific probe which is complementary to said second probe, and said released second beads bind without presence of said transport first beads with said capacitive sensor immobilized probes,
    wherein said second beads are released from said first beads by heating before sensing, or
    said target microbiological entity includes nucleic acid, and peptide nucleic acid probes complementary to those on said second beads are used to release said tethered second beads from said first beads;
    detecting with said capacitive sensor a number of said released second beads to provide capacitance data; and
    processing said capacitance data to quantify presence of said target microbiological entity in said crude sample,
    wherein at least some of said second beads are adapted to degenerate over said capacitive sensor with application of heat to the extent that at least some of said second beads become integral.

2. The method as claimed in claim 1, wherein said tethered second beads are released from said first beads by heating.

3. The method as claimed in claim 1, wherein said tethered second beads are released from said first beads by heating by sensor on-chip or under-chip heaters.

4. The method as claimed in claim 1, wherein said second probe comprises peptide nucleic acid probes.

5. The method as claimed in claim 1, wherein said capacitive sensor has an analyte channel and a negative channel and said capacitive sensor is calibrated so that the same capacitance is detected in both said analyte and negative channels if there is no target microbiological entity present.

6. The method as claimed in claim 1, wherein said second beads have a size in the range of 0.5 µm to 5 µm.

7. The method as claimed in claim 1, wherein said microbiological entity is a nucleic acid and multiple target nucleic acids or loci are targeted, in which:
    a. for genes or loci A, B and C: $1_A+1_B+1_C=X3$ signal
    b. for genes or loci A and B: $2A+2_B=X2$ signal;
    wherein the method does not distinguish between multiple genes such as A, B and C and assumes that each confer equal information about the question of interest;
    wherein A, B and C are single nucleotide polymorphisms, which are all considered to be equally desirable in an animal bred for a correlated trait, and said capacitive sensor response is calibrated to indicate if said animal is likely to have a particular characteristic; and
    wherein the combination of genes represent known mutations, which are liable to lead to a particular genetic disease.

8. The method of claim 7, wherein said correlated trait is milk production and said characteristic is milk yield.

9. The method as claimed in claim 1, wherein multiple target nucleic acids are targeted and second bead reverse loci bind to each of the respective nucleic acids; and wherein said second bead reverse loci are selected to provide additional sequence specificity to that conferred by said first beads but primarily amplify a signal for each nucleic acid captured by a first bead of said first beads; and wherein said second bead reverse loci are distinguished from each other downstream using different immobilized second probes on different sensors.

10. The method as claimed in claim 1, wherein said second probe is a peptide nucleic acid probe and said peptide nucleic acid probe attaches to said target microbiological entity by nucleic acid during cell lysis.

11. The method as claimed in claim 1, wherein said target microbiological entity includes nucleic acid, and wherein peptide nucleic acid probes complementary to those on said second beads are used to separate said tethered second beads from said first beads.

12. The method as claimed in claim 1, wherein said microbiological entity includes nucleic acid, and wherein peptide nucleic acid probes complementary to those on said second beads are used to separate said tethered first beads and second beads; and wherein said separation is performed at approximately room temperature.

13. The method as claimed in claim 1, wherein:
said second beads are stable in aqueous solution but break down when moved into said aqueous solution over said capacitive sensor, and/or
said second beads contain elements, which change a capacitance of said solution, and/or
breakdown of said second beads releases a fine debris of particles, which increases a change in a capacitance immediately over said surface of said capacitive sensor.

14. The method as claimed in claim 1, wherein said microbiological entity is a nucleic acid and an anti-sense strand is targeted such that non-complementary forward probes target different loci on a sense strand and said anti-sense strand of a same gene, and in which both said sense and anti-sense strands are captured from said crude sample.

15. The method as claimed in claim 1, wherein a sequence-specific forward locus is used for said first bead tethering to a nucleic acid in said crude sample and multiple second bead reverse loci are used.

16. The method as claimed in claim 1, wherein said first probe includes a peptide nucleic acid probe and said first beads with an attached target nucleic acid are introduced to said second vessel containing deionized water and said second beads.

17. The method as claimed in claim 1, wherein a size of said second beads is less than half a size of said first beads.

18. The method as claimed in claim 1, wherein said second beads have a size in the range of 1.0 µm to 3.0 µm.

19. The method as claimed in claim 1, wherein a size of said second beads is about 1.0 µm and a size of said first beads is about 2.8 µm.

20. The method as claimed in claim 1, wherein said target microbiological entity includes nucleic acid, and wherein peptide nucleic acid probes complementary to those on said second beads or said first beads displace said nucleic acid due to preferential peptide nucleic acid-to-peptide nucleic acid binding to release said nucleic acid and so to release said tethered second beads from said first beads.

21. The method as claimed in claim 1, wherein said entity comprises multiple target nucleic acids or loci and second bead reverse loci bind to each of a respective target nucleic acid.

22. The method as claimed in claim 1, wherein said second beads comprises a mix of second beads, and said capacitive sensor comprises said plurality of immobilized probes, each of which has said unique sequence-specific probe which is complementary to each of said second probes on each of said second beads, and which each bind to their complementary immobilized probe.

23. The method as claimed in claim 1, wherein said detecting with said capacitive sensor further comprises providing capacitance data both before and after the liquid medium evaporates.

* * * * *